United States Patent [19]

Metz et al.

[11] 4,246,264

[45] Jan. 20, 1981

[54] TREATMENT OF HYPERURICAEMIA WITH ETOFYLLINE CLOFIBRATE

[75] Inventors: Gunter Metz; Manfred Specker, both of Blaubeuren, Fed. Rep. of Germany

[73] Assignee: Ludwig Merckle, K.G., Chem. Pharm. Fabrik, Fed. Rep. of Germany

[21] Appl. No.: 112,907

[22] Filed: Jan. 17, 1980

[51] Int. Cl.$^3$ ............................................ A61K 31/52
[52] U.S. Cl. ..................................................... 424/253
[58] Field of Search ........................................ 424/253

[56] References Cited

U.S. PATENT DOCUMENTS 3,984,413  10/1976  Metz et al. ............................ 424/253

Primary Examiner—Frederick E. Waddell
Attorney, Agent, or Firm—Roylance, Abrams, Berdo & Farley

[57] ABSTRACT

The use of etofylline clofibrate for the treatment of elevated serum levels of uric acid in humans is disclosed.

7 Claims, No Drawings

TREATMENT OF HYPERURICAEMIA WITH ETOFYLLINE CLOFIBRATE

BACKGROUND OF THE INVENTION

1. Field of the Invention

This invention relates to a new use for a known pharmaceutical compound. More specifically, this invention relates to the use of etofylline clofibrate for the treatment of elevated uric acid levels (hyperuricaemia).

2. Description of the Prior Art 1-(7-Theophyllinyl)-2-ethyl-[2-(p-chlorphenoxy)-isobutyrate], otherwise known as etofylline clofibrate, having the formula:

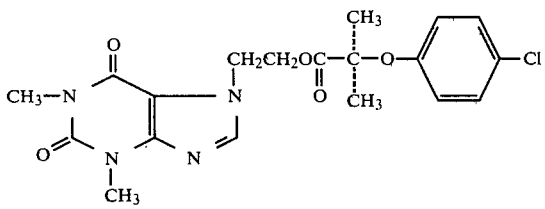

is disclosed in U.S. Pat. No. 3,984,413 as offering excellent antilipemic and anticholesterolemic properties as well as pronounced peripheral and vasodilative effect. However, its use in the treatment of hyperuricaemia is not known.

SUMMARY OF THE INVENTION

It has now been discovered that etofylline clofibrate is useful in the treatment of hyperuricaemia. By "hyperuricaemia" is meant elevated serum uric acid levels exceeding normal limits of from 2.5–7.0 mg. % for men and from 1.5–6.0 mg. % for women. In various clinical trials on the treatment of hyperlipemic patients, this drug offered pronounced advantages compared to the standard drug clofibrate.

In toxicology and pharmacology, etofylline clofibrate was superior to clofibrate and in clinical trials equal antilipemic potency in much less dosage was found, compared to the effect under the usual dosage of clofibrate of 1.5 g/day.

In accordance with the practice of this invention, there is administered to a host animal, including man, which is afflicted with hyperuricaemia, a drug comprising this compound. The drug is administered orally in an amount sufficient to lower the serum uric acid level of said host.

The drug may be administered in the form of, e.g., soft or hard gelatin capsules in doses of from 250 to 1250 mg./day, and, preferably, 500 to 750 mg./day. The drug may be administered in single doses of 250 to 600 mg./unit and preferably, 250 to 300 mg./unit. The suggested daily dosage for oral administration is 1 to 4 and preferably 2 to 3 soft or hard gelatin capsules containing 250 to 300 mg. of etofylline clofibrate.

DESCRIPTION OF THE PREFERRED EMBODIMENTS

The following examples serve to illustrate the practice of this invention. In these examples, serum uric acid levels were determined in accordance with usual determinations of the clinical laboratory. The limits of serum uric acid, given above, are normal standards in medicinal practice. The statistical significance was calculated using the more specific frequency of the individual changes compared to the values of entrance.

EXAMPLE 1

Hard gelatin capsules containing 250 mg. of etofylline clofibrate per capsule were administered at the rate of three capsules per day over a 6-day period to a group of 12 healthy volunteers. The group consisted of 5 men and 7 women and, besides one man having a serum level below the normal limit, all uric acid levels were within the norm. The uric acid levels were determined in all volunteers before beginning (day 0), after 2, 4 and 6 days of treatment.

| Frequency | Day 2 | Day 4 | Day 6 |
|---|---|---|---|
| Increase (+) | 1 | 1 | 2 |
| Unchanged (0) | 0 | 1 | 0 |
| Decrease (−) | 10 | 9 | 9 |
| Significance P = | 0.05 | 0.05 | 0.05 |

These results show that etofylline clofibrate has a significant uric acid lowering efficacy, even in normal humans and in short-term administration.

EXAMPLE 2

Etofylline clofibrate was tested in 5 different clinical studies in a total of 231 patients, mainly suffering from hyperlipemia and other metabolic disorders, including 73 patients with elevated levels of uric acid. The drug was administered in dosages of 2 or 3 capsules daily over a period of 2 to 5 months, each capsule containing 250 mg. of etofylline clofibrate.

For the statistical biometric evaluation of the effect on uric acid levels, the data of the hyperuricaemic patients were separately evaluated. The results are summarized in Table 1.

TABLE 1

| Study | Patients[1] Number | % | Dosage capsules daily | Treatment month | Frequency increase (+) | unchanged (0) | decrease (−) | Significance P |
|---|---|---|---|---|---|---|---|---|
| I | 11 | 22 | 3 | 1 | 1 | 0 | 10 | 0.05 |
|   |    |    |   | 2 | 2 | 0 | 9  | 0.05 |
| II | 11 | 22 | 2 | 1 | 1 | 0 | 10 | 0.05 |
|   |    |    |   | 2 | 1 | 0 | 10 | 0.05 |
| III | 19 | 46 | 2 | 1 | 0 | 0 | 19 | 0.05 |
|   |    |    | 3 | 3 | 3 | 2 | 14 | 0.05 |
|   |    |    | 3 | 5[2] | 0 | 0 | 14 | 0.05 |
| IV | 29[3] | 48 | 3 | 2 | 6 | 0 | 21 | 0.05 |
| V | 3 | 15 | 3 | 1 | 0 | ·0 | 3 | 0.05 |
|   |   |    |   | 2 | 0 | 0 | 3 | 0.05 |

[1]Patients with elevated serum uric acid levels and % of total group.
[2]After 3 months of treatment, 5 patients dropped out due to severe disorders of heart and circulation.
[3]For 2 patients, final values were not reported.

As can be seen from the results with he hyperuricaemic patients at the end of the treatment period (2 or 5 months), there was an increase of uric acid levels in only 9 patients, while in 57 patients a significant decrease was measurable.

It is thus apparent that etofylline clofibrate offers an uricosuric effect. This was demonstrated in the clinical studies II and III by measurement of an increase of uric acid levels in the urine, and also in the test of Example 1 in volunteers, where the efficacy of etofylline clofibrate is very similar to that of the standard uricosuric benzbromarone.

We claim:

1. A process for the treatment of a host animal which is afflicted with hyperuricaemia which comprises administering to said animal an amount sufficient to lower the serum uric acid level of said host animal, a drug comprising etofylline clofibrate.

2. A process as defined in claim 1 wherein said host animal is a human being.

3. A process as defined in claim 2 wherein said drug is administered in the form of a soft or hard gelatin capsule.

4. A process as defined in claim 2 wherein said drug is administered in a dose of 250 to 1250 mg./day.

5. A process as defined in claim 2 wherein said drug is administered in a dose of 500 to 750 mg./day.

6. A process as defined in claim 2 wherein said drug is administered in a single dose of 250 to 600 mg./unit.

7. A process as defined in claim 2 wherein said drug is administered in a single dose of 250 to 300 mg./unit.

* * * * *